(12) United States Patent
Allison

(10) Patent No.: US 10,233,625 B1
(45) Date of Patent: Mar. 19, 2019

(54) MOTION SENSOR CONTROLLED TOILET TANK AIR FILTER

(71) Applicant: Jeffrey Allison, Houston, TX (US)

(72) Inventor: Jeffrey Allison, Houston, TX (US)

( * ) Notice: Subject to any disclaimer, the term of this patent is extended or adjusted under 35 U.S.C. 154(b) by 0 days.

(21) Appl. No.: 15/590,794

(22) Filed: May 9, 2017

(51) Int. Cl.
　　E03D 9/02　　(2006.01)
　　E03D 9/00　　(2006.01)
　　A61L 9/12　　(2006.01)

(52) U.S. Cl.
　　CPC .............. *E03D 9/007* (2013.01); *A61L 9/122* (2013.01)

(58) Field of Classification Search
　　CPC ............................................... E03D 2009/024
　　USPC ..................................... 4/222–233
　　See application file for complete search history.

(56) References Cited

U.S. PATENT DOCUMENTS

| | | | |
|---|---|---|---|
| 2,846,696 A | 8/1958 | Herrioll | |
| 4,317,242 A | 3/1982 | Stamper | |
| 6,041,449 A | 3/2000 | Brown et al. | |
| 6,209,146 B1 * | 4/2001 | Gonzalez | E03D 9/05 4/209 R |
| 6,279,173 B1 * | 8/2001 | Denzin | E03D 9/05 4/213 |
| 6,610,121 B2 * | 8/2003 | Chasen | A61L 9/12 261/115 |
| 6,643,850 B2 * | 11/2003 | Chasen | E03D 9/052 4/213 |
| D507,046 S | 7/2005 | Hickman | |
| 6,948,192 B2 * | 9/2005 | Hipponsteel | E03D 9/05 4/213 |
| 7,797,766 B2 | 9/2010 | Ellinger | |
| 8,337,602 B2 | 12/2012 | Foerster | |
| 8,709,137 B2 * | 4/2014 | Chan | A61L 2/022 4/306 |

\* cited by examiner

*Primary Examiner* — Lori Baker

(57) ABSTRACT

A battery-operated motion sensor controlled toilet tank air filter including a pair of exhaust housing bodies and an attachment bracket to hang the exhaust housing bodies from the upper sides of a toilet tank and to house a centrally disposed motion sensor, which upon detection of motion, activates a single transmitter operationally communicating therewith. The transmitter then activates a motor disposed within each housing body to operate a respective fan, which directs airflow drawn in through a respective louvered air inlet port through a pair of compartments containing an activated charcoal air filter and a scented air filter therein, and subsequently out through an air exhaust port to provide clean and scented air in the bathroom.

5 Claims, 5 Drawing Sheets

MOTION SENSOR CONTROLLED TOILET TANK AIR FILTER

BACKGROUND OF THE INVENTION

Various types of toilet odor control devices provided to ventilate, filter, deodorize, scent, or filter the air surrounding the toilet are known in the prior art. However, what is needed, and what the present device provides, is a battery-operated motion sensor controlled toilet tank air filter including a pair of exhaust housing bodies and an attachment bracket to hang the exhaust housing bodies from the upper sides of a toilet tank and to house a centrally disposed motion sensor. Upon detection of motion, the motion sensor activates a single transmitter operationally communicating therewith. The transmitter then activates a motor disposed within each housing body to operate a respective fan, which directs airflow drawn in through a respective louvered air inlet port through a pair of compartments containing an activated charcoal air filter and a scented air filter therein, and subsequently out through an air exhaust port to provide clean and scented air in the bathroom.

FIELD OF THE INVENTION

The present invention relates to a motion sensor controlled toilet tank air filter.

SUMMARY OF THE INVENTION

The general purpose of the present motion sensor controlled toilet tank air filter, described subsequently in greater detail, is to provide a motion sensor controlled toilet tank air filter which has many novel features that result in a motion sensor controlled toilet tank air filter which is not anticipated, rendered obvious, suggested, or even implied by prior art, either alone or in combination thereof.

To accomplish this, the present motion sensor controlled toilet tank air filter includes a pair of exhaust housing bodies and an attachment bracket to hang the exhaust housing bodies from the upper sides of a toilet tank. Each of the pair of exhaust housing bodies has an air inlet port, with a plurality of convex louvers, disposed on a front end thereof. The convex shape of each of the louvers is provided to prevent moisture from entering the exhaust housing bodies. A motorized bladed fan is disposed therein in a position proximal the front end of each exhaust housing body and a receiver is disposed on and in operational communication with the respective motor. Each of a first compartment and a second compartment is transversely disposed within each of the pair of exhaust housing bodies and is accessed through a slot in the respective outer wall. A pair of air filters is provided for each of the exhaust housing bodies and includes an activated charcoal air filter and a scented air filter removably disposed within the first compartment and the second compartment, respectively. The activated charcoal filter is provided to adsorb unwanted odorous substances. The scented air filter is provided to permit the fan to circulate a desired scent within the bathroom in which the toilet is located. A rechargeable lithium battery provides a source of power for each of the respective motor and receiver. An air exhaust port and a charging port for the battery are disposed on the rear end of each of the pair of exhaust housing bodies. A motion sensor is centrally disposed on the forward side of a crossmember of the attachment bracket. A transmitter is disposed on the rearward side of crossmember and is directly adjacent and in operational communication with the motion sensor. Upon detection of motion by the motion sensor, the transmitter, the receiver, the motor, and the fan of each of the exhaust housing bodies are activated to direct airflow into each of the pair of exhaust housing bodies through the air inlet port, through the first compartment and the air filter therein subsequent to the air inlet port, through the second compartment and the air filter therein subsequent to the first compartment, and out of each of the pair of exhaust housing bodies through the respective air exhaust port. The motion sensor is deactivated upon the lack of movement for detection by the motion sensor. Upon deactivation of the motion sensor, the transmitter along with the receiver, the motor, and the fan disposed within each of the exhaust housing bodies are deactivated.

Thus has been broadly outlined the more important features of the present motion sensor controlled toilet tank air filter so that the detailed description thereof that follows may be better understood and in order that the present contribution to the art may be better appreciated.

BRIEF DESCRIPTION OF THE DRAWINGS

Figures

DETAILED DESCRIPTION OF THE DRAWINGS

Figure 1:
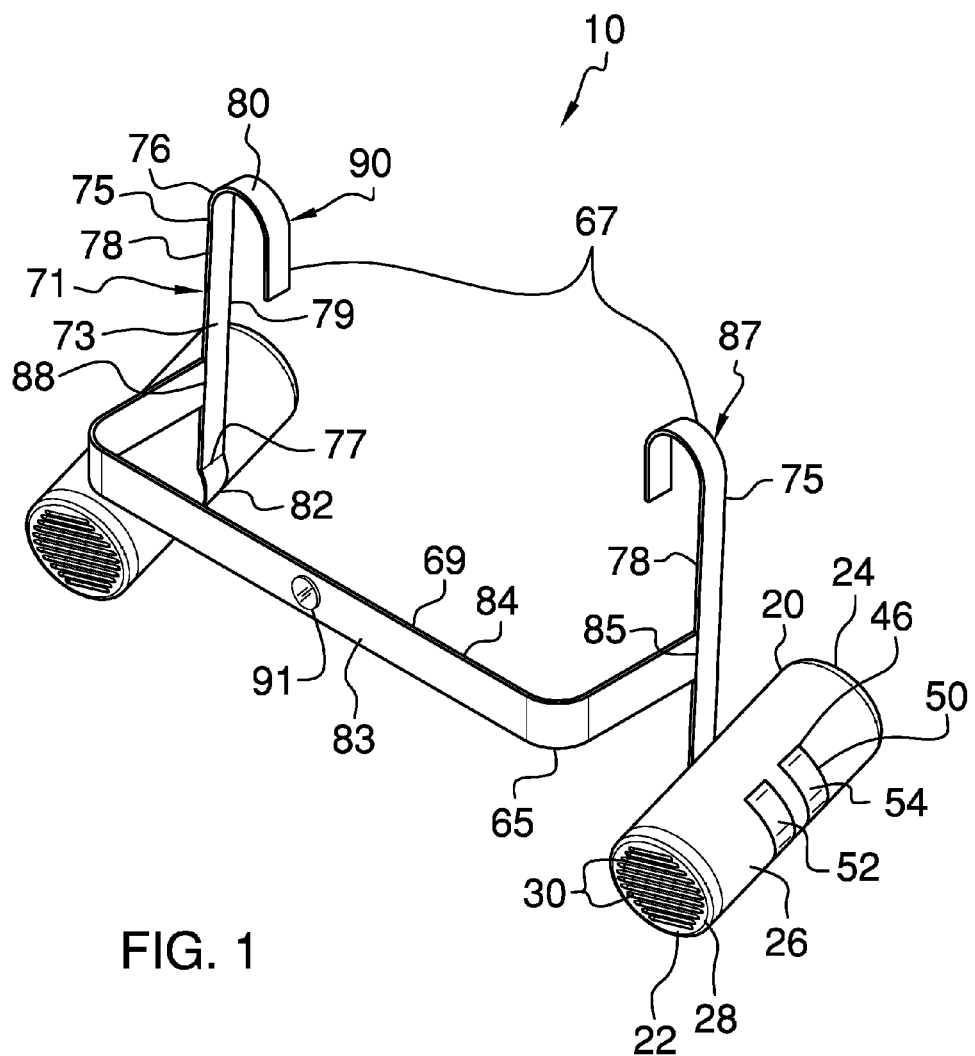
FIG. 1 is an isometric view.
Figure 2:
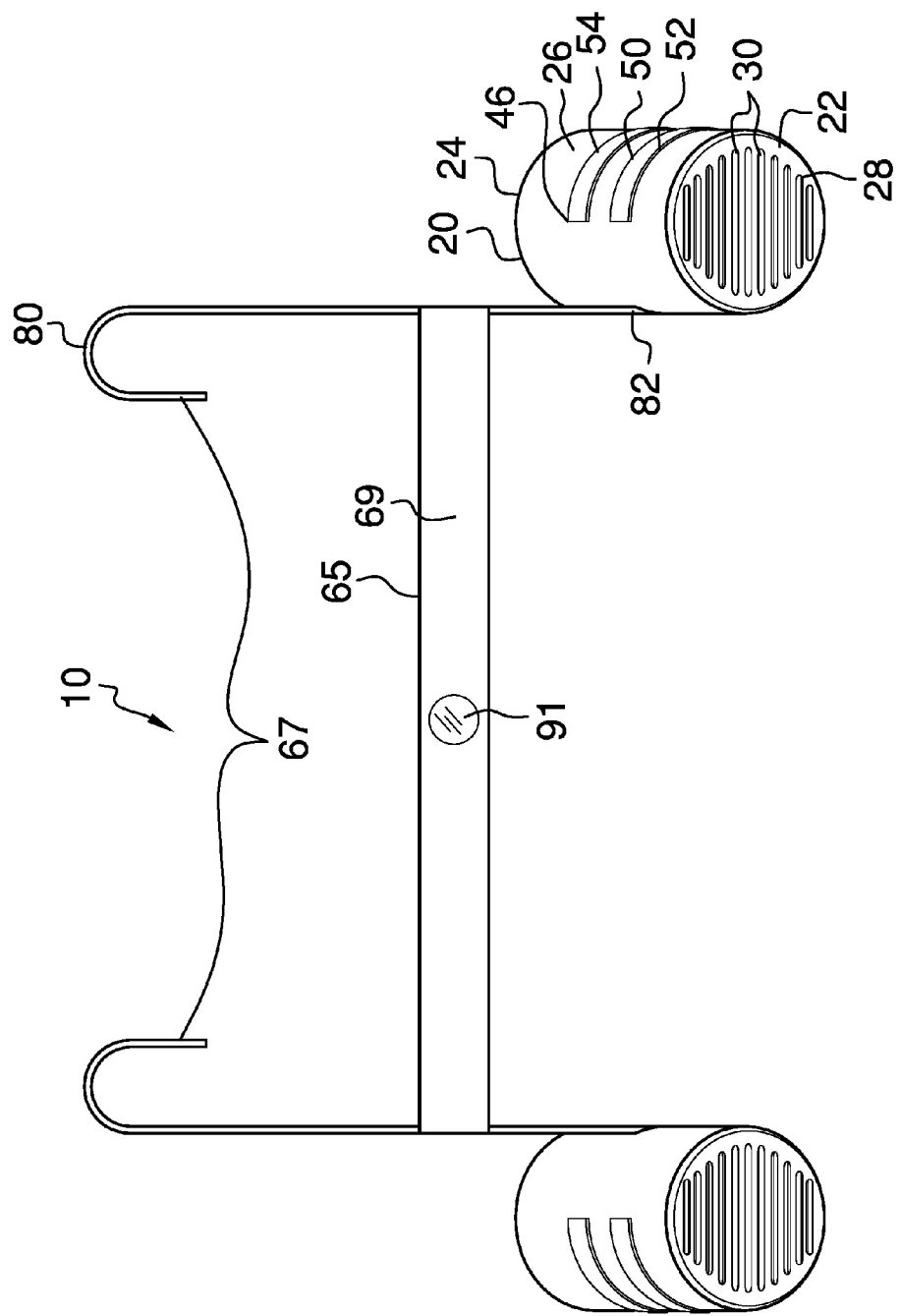
FIG. 2 is a front elevation view.
Figure 3:
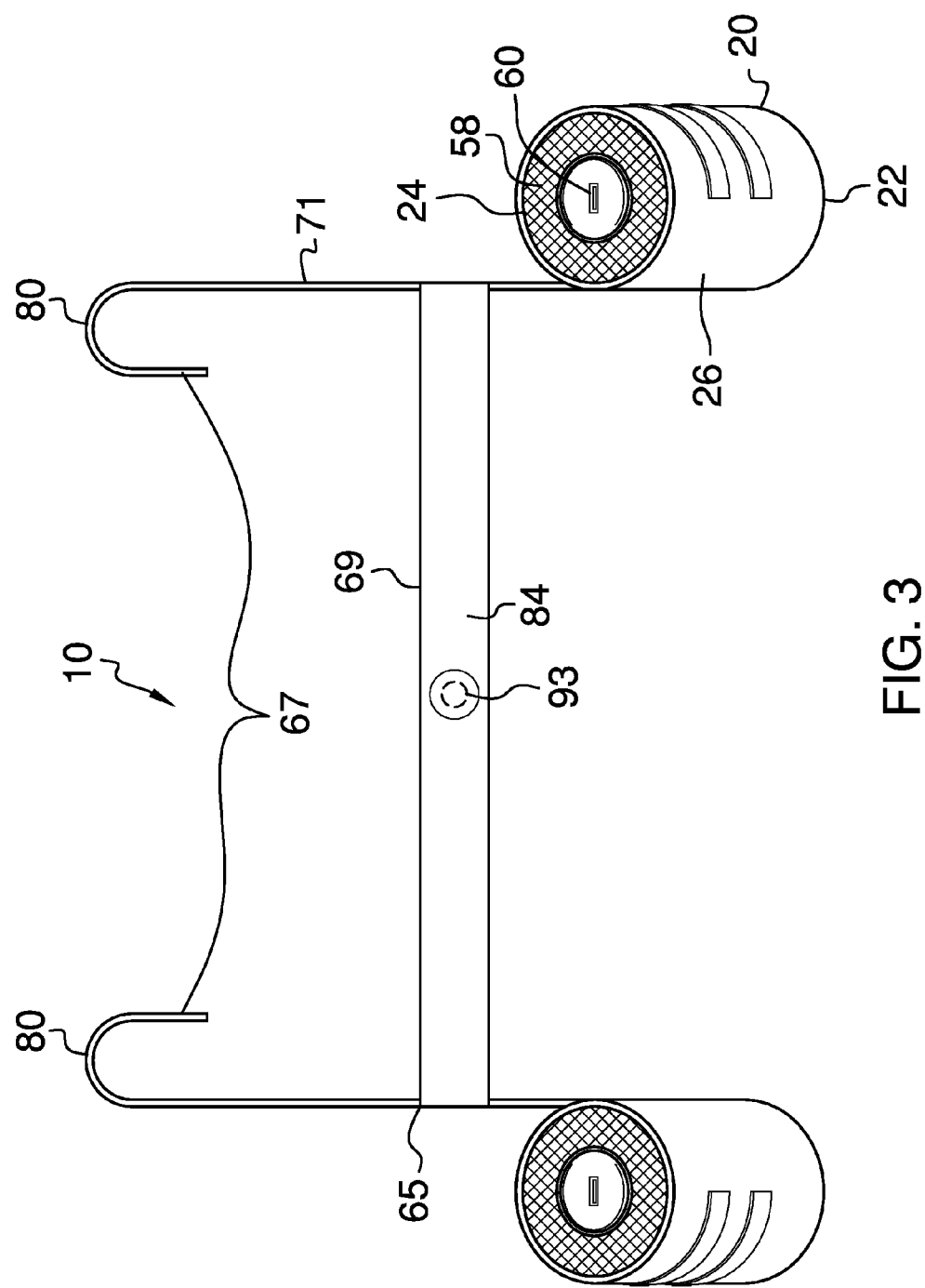
FIG. 3 is a rear elevation view.
Figure 4:
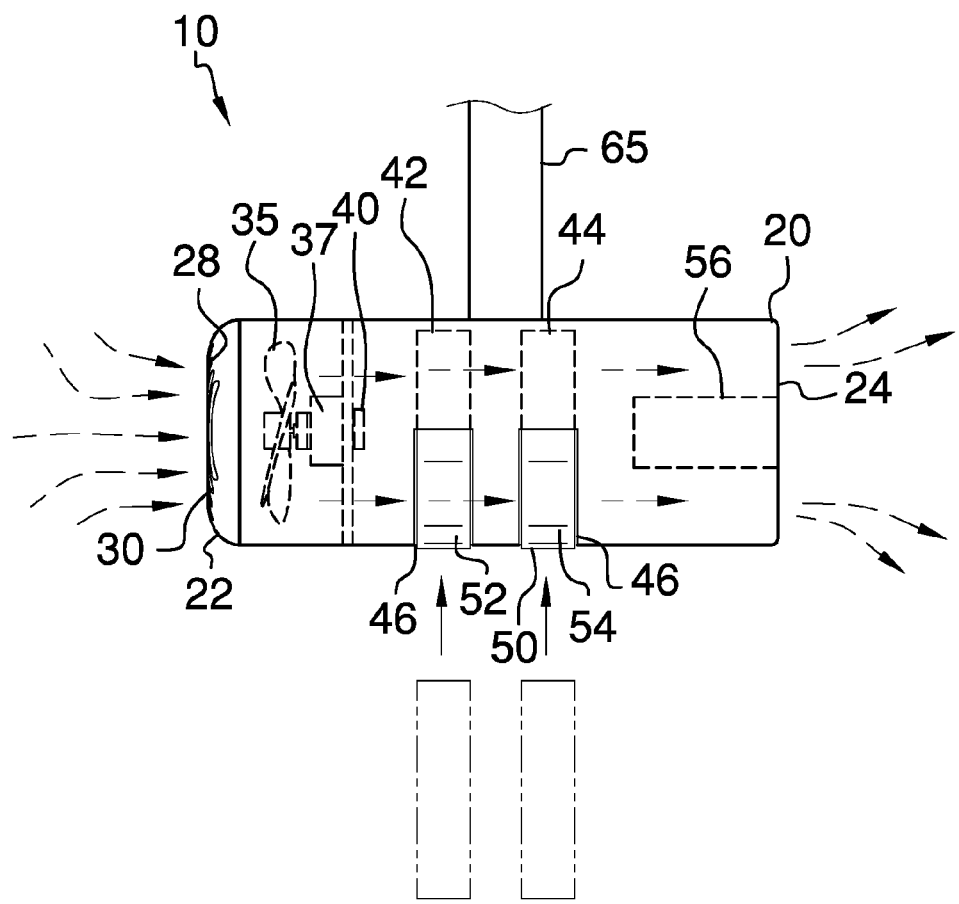
FIG. 4 is a side elevation view.
Figure 5:
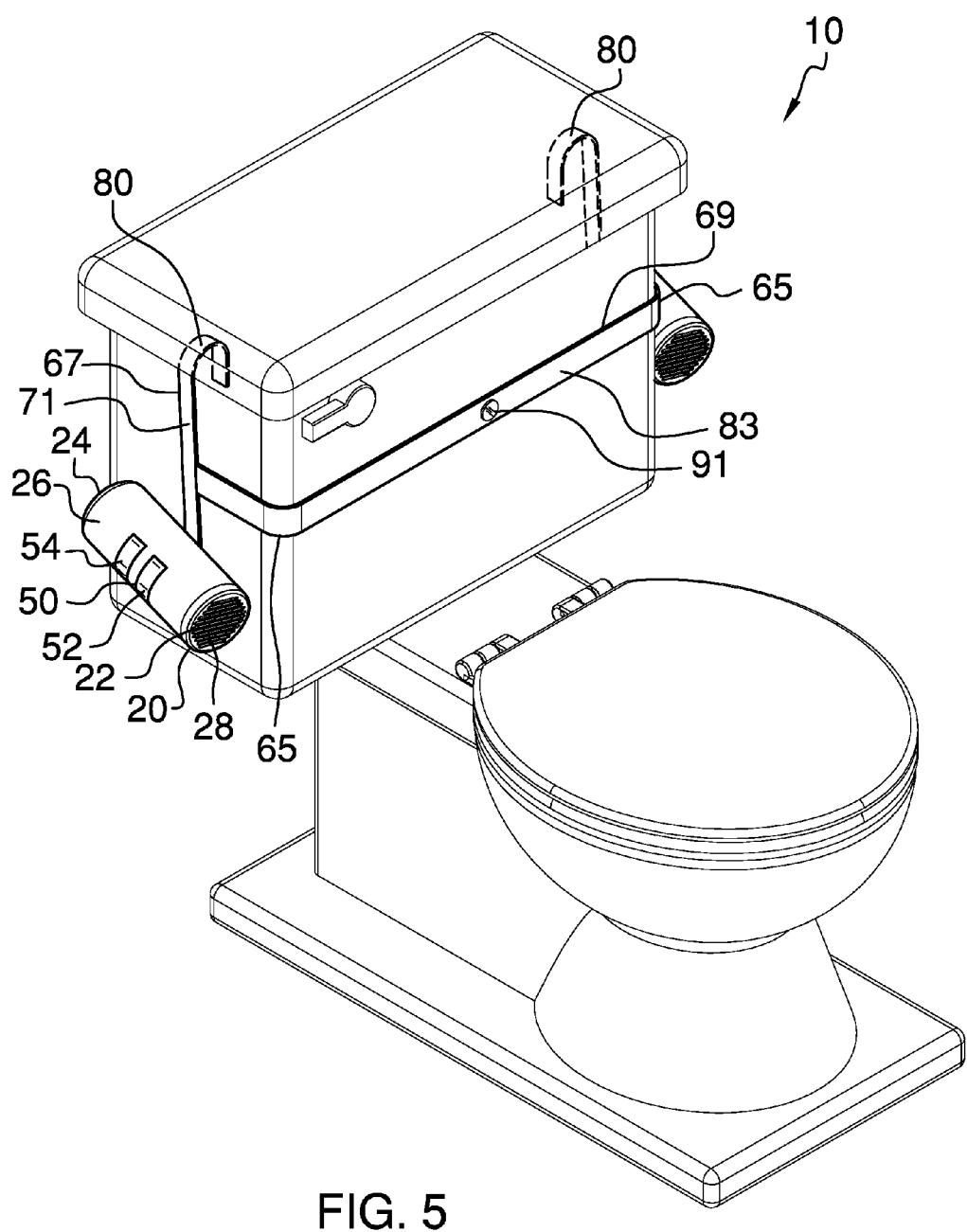
FIG. 5 is an in-use perspective view.

With reference now to the drawings, and in particular FIGS. 1 through 5 thereof, an example of the instant motion sensor controlled toilet tank air filter employing the principles and concepts of the present motion sensor controlled toilet tank air filter and generally designated by the reference number 10 will be described.

Referring to FIGS. 1 through 5 the present motion sensor controlled toilet tank air filter 10 is illustrated. The motion sensor controlled toilet tank air filter 10 includes a pair of exhaust housing bodies 20. Each of the pair of exhaust housing bodies 20 has a front end 22, a rear end 24, and an outer wall 26 continuously disposed between the front end 22 and the rear end 24. Each of the pair of exhaust housing bodies 20 includes an air inlet port 28 disposed on the front end 22. The air inlet port 28 includes a plurality of convex louvers 30. Each of the pair of exhaust housing bodies 20 also includes a bladed fan 35 disposed therein in a position proximal the front end 22 and a motor 37 therein in a position directly adjacent and in operational communication with the bladed fan 35. A receiver 40 is disposed on the respective motor 37 and is in operational communication therewith. A first compartment 42 is transversely disposed within each of the pair of exhaust housing bodies 20 in a position proximal the receiver 40. A second compartment 44 is transversely disposed within each of the pair of exhaust housing bodies 20 in a position proximal the first compartment 42. Each of the exhaust housing bodies 20 also includes a pair of slots 46 disposed in the respective outer wall 26 to provide access to the respective one of the first compartment 42 and the second compartment 44. One of the pair of slots 46 is directly adjacent to a respective one of the first compartment 42 and the second compartment 44. Each of the first compartment 42 and the second compartment 44 is configured to removably receive an air filter 50 therein.

A pair of the air filters 50 is provided for each of the exhaust housing bodies 20 and includes an activated charcoal air filter 52 removably disposed within the first compartment 42 and a scented air filter 54 removably disposed within the second compartment 44. The activated charcoal filter 52 is provided to adsorb unwanted odorous substances. The scented air filter 54 is provided to permit the fan 35 to circulate a desired scent within the bathroom in which the toilet is located.

A rechargeable battery 56, which can be a rechargeable lithium battery, is disposed within each of the exhaust housing bodies 20 and is in operational communication with each of the respective motor 37 and receiver 40. In addition, each of the exhaust housing bodies 20 includes an air exhaust port 58 disposed on the rear end 24 and a charging port 60 centrally disposed on the rear end 24. The charging port 60 is provided to operationally connect a host power source to the rechargeable battery 56.

An attachment bracket 65 is provided to hang each of the pair of exhaust housing bodies 20 onto a respective upper side of a toilet tank. The attachment bracket 65 includes a pair of S-hooks 67 connected together by a crossmember 69. Each S-hook 67 has a central section 71 having an interior side 73, an exterior side 75, a top side 76, a bottom side 77, a front side 78, a rear side 79, a top hook 80 disposed on the interior side 73 and being directed downwardly toward the bottom side 77, and a convex bottom extension 82 disposed on the exterior side 75 and being directed upwardly toward the top side 76. The bottom extension 82 is attached to a respective one of the pair of exhaust housing bodies 20. The crossmember 69 is a squared C-shaped crossmember and has a forward side 83, a rearward side 84, a right end 85 centrally disposed on a front side 78 of a right S-hook 87 of the pair of S-hooks 65 and a left end 88 centrally disposed on a front side 78 of a left S-hook 90 of the pair of S-hooks 67.

A motion sensor 91 is centrally disposed on the forward side 83 of the crossmember 69. A transmitter 93 is disposed on the rearward 84 of the crossmember 69 in a position directly adjacent and in operational communication with the motion sensor 91. Upon detection of motion by the motion sensor 91, the motion sensor 91 activates the transmitter 93. Upon activation of the transmitter 93, the transmitter 93 activates the receiver 40 within each of the exhaust housing bodies 20. Upon activation of the receiver 40, the receiver 40 activates the motor 37. Upon activation of the motor 37, the motor 37 activates the fan 35 and upon activation of the fan 46, the fan 35 directs airflow into each of the pair of exhaust housing bodies 20 through the air inlet port 28, through the first compartment 42 and the air filter 50 therein subsequent to the air inlet port 28, through the second compartment 44 and the air filter 50 therein subsequent to the first compartment 42, and out of each of the pair of exhaust housing bodies 20 through the respective air exhaust port 58. The motion sensor 91 is deactivated upon the lack of movement for detection by the motion sensor 91. Upon deactivation of the motion sensor 91, the transmitter 93 as well as the receiver 40, the motor 37, and the fan 35 disposed within each of the exhaust housing bodies 20 are deactivated.

What is claimed is:

1. A motion sensor controlled toilet tank air filter comprising:
   a pair of housing bodies, each of the pair of housing bodies having a front end, a rear end, and an outer wall continuously disposed between the front end and the rear end, each of the pair of exhaust housing bodies comprising:
   an air inlet port disposed on the front end, the air inlet port having a plurality of louvers;
   a bladed fan disposed therein in a position proximal the front end;
   a motor disposed therein in a position directly adjacent the bladed fan, the motor being in operational communication with the bladed fan;
   a receiver disposed on the respective motor, the receiver being in operational communication with the respective motor;
   a first compartment transversely disposed therein in a position proximal the receiver;
   a second compartment transversely disposed therein in a position proximal the first compartment;
   a pair of slots disposed in the outer wall, one of the pair of slots being directly adjacent to a respective one of the first compartment and the second compartment;
   wherein each of the first compartment and the second compartment is configured to removably receive an air filter therein;
   a rechargeable battery disposed therein, the rechargeable battery being in operational communication with each of the motor and the receiver;
   an air exhaust port disposed on the rear end;
   a charging port centrally disposed on the rear end, wherein the charging port operationally connects a host power source to the rechargeable battery;
   an attachment bracket configured to attach each of the pair of exhaust housing bodies to a respective upper side of a toilet tank, the attachment bracket comprising:
   a pair of S-hooks, each of the pair of S-hooks having a central section having an interior side, an exterior side, a top side, a bottom side, a front side, a rear side, a top hook disposed on the interior side and being directed downwardly toward the bottom side, a convex bottom extension disposed on the exterior side and being directed upwardly toward the top side;
   wherein the bottom extension is attached to the respective one of the pair of housing bodies;
   a square C-shaped crossmember, the crossmember having a forward side, a rearward side, a right end centrally disposed on a front side of a right S-hook of the pair of S-hooks and a left end centrally disposed on a front side of a left S-hook of the pair of S-hooks;
   a motion sensor centrally disposed on the forward side of the crossmember; and
   a single transmitter disposed on the rearward side of the crossmember in a position directly adjacent the motion sensor, the transmitter being in operational communication with the motion sensor;
   wherein upon detection of motion by the motion sensor, the motion sensor activates the transmitter;
   wherein upon activation of the transmitter, the transmitter activates the receiver within each of the exhaust housing bodies;
   wherein upon activation of the receiver, the receiver activates the respective motor;
   wherein upon activation of the motor, the motor activates the respective fan and upon activation of the fan, the fan directs airflow into the respective one of the pair of exhaust housing bodies through the air inlet port, through the first compartment subsequent to the air inlet port, through the second compartment subsequent to the first compartment, and out of each of the pair of exhaust housing bodies through the respective air exhaust port;

wherein the motion sensor is deactivated upon the lack of movement for detection by the motion sensor; and wherein upon deactivation of the motion sensor, the transmitter and the receiver, the motor, and the fan disposed within each of the exhaust housing bodies are deactivated.

2. The motion sensor controlled toilet tank air filter of claim 1 comprising a pair of air filters comprising an activated charcoal air filter removably disposed within the first compartment and a scented air filter removably disposed within the second compartment.

3. The motion sensor controlled toilet tank air filter of claim 1 wherein each of the plurality of louvers is convex.

4. The motion sensor controlled toilet tank air filter of claim 1 wherein the rechargeable battery is a rechargeable lithium battery.

5. A motion sensor controlled toilet tank air filter comprising:
  a pair of housing bodies, each of the pair of housing bodies having a front end, a rear end, and an outer wall continuously disposed between the front end and the rear end, each of the pair of exhaust housing bodies comprising:
    an air inlet port disposed on the front end, the air inlet port having a plurality of convex louvers;
    a bladed fan disposed therein in a position proximal the front end;
    a motor disposed therein in a position directly adjacent the bladed fan, the motor being in operational communication with the bladed fan;
    a receiver disposed on the respective motor, the receiver being in operational communication with the respective motor;
    a first compartment transversely disposed therein in a position proximal the receiver;
    a second compartment transversely disposed therein in a position proximal the first compartment;
    a pair of slots disposed in the outer wall, one of the pair of slots being directly adjacent to a respective one of the first compartment and the second compartment;
    wherein each of the first compartment and the second compartment is configured to removably receive an air filter therein;
    a pair of air filters comprising an activated charcoal air filter removably disposed within the first compartment and a scented air filter removably disposed within the second compartment a rechargeable lithium battery disposed therein, the rechargeable lithium battery being in operational communication with each of the motor and the receiver;
    an air exhaust port disposed on the rear end;
    a charging port centrally disposed on the rear end, wherein the charging port operationally connects a host power source to the rechargeable battery;
  an attachment bracket configured to attach each of the pair of exhaust housing bodies to a respective upper side of a toilet tank, the attachment bracket comprising:
    a pair of S-hooks, each S-hook having a central section having an interior side, an exterior side, a top side, a bottom side, a front side, a rear side, a top hook disposed on the interior side and being directed downwardly toward the bottom side, a convex bottom extension disposed on the exterior side and being directed upwardly toward the top side;
    wherein the bottom extension is attached to a respective one of the pair of housing bodies;
    a square C-shaped crossmember, the crossmember having a forward side, a rearward side, a right end centrally disposed on a front side of a right S-hook of the pair of S-hooks and a left end centrally disposed on a front side of a left S-hook of the pair of S-hooks;
    a motion sensor centrally disposed on the forward side of the crossmember; and
    a single transmitter disposed on the rearward side of the crossmember in a position directly adjacent the motion sensor, the transmitter being in operational communication with the motion sensor;
  wherein upon detection of motion by the motion sensor, the motion sensor activates the transmitter;
  wherein upon activation of the transmitter, the transmitter activates the receiver within each of the exhaust housing bodies;
  wherein upon activation of the receiver, the receiver activates the respective motor;
  wherein upon activation of the motor, the motor activates the respective fan and upon activation of the fan, the fan directs airflow into the respective one of the pair of exhaust housing bodies through the air inlet port, through the first compartment and the activated charcoal air filter therein subsequent to the air inlet port, through the second compartment and the scented air filter subsequent to the first compartment, and out of each of the pair of exhaust housing bodies through the respective air exhaust port;
  wherein the motion sensor is deactivated upon the lack of movement for detection by the motion sensor; and
  wherein upon deactivation of the motion sensor, the transmitter and the receiver, the motor, and the fan disposed within each of the exhaust housing bodies are deactivated.

* * * * *